US009448242B2

(12) United States Patent
Eschalier et al.

(10) Patent No.: US 9,448,242 B2
(45) Date of Patent: Sep. 20, 2016

(54) USE OF K2P POTASSIUM CHANNEL ACTIVATORS AS ANTALGICS

(75) Inventors: Alain Eschalier, Chamalieres (FR); Jérôme Busserolles, Saulzet (FR); Abdelkrim Alloui, Clermont Ferrand (FR); Michel Lazdunski, Nice (FR)

(73) Assignee: UNIVERSITE D'AUVERGNE CLERMONT I, Clermont Ferrand (FR)

( * ) Notice: Subject to any disclaimer, the term of this patent is extended or adjusted under 35 U.S.C. 154(b) by 0 days.

(21) Appl. No.: 13/497,353

(22) PCT Filed: Sep. 21, 2010

(86) PCT No.: PCT/FR2010/051968
§ 371 (c)(1),
(2), (4) Date: Jun. 25, 2012

(87) PCT Pub. No.: WO2011/033241
PCT Pub. Date: Mar. 24, 2011

(65) Prior Publication Data
US 2012/0260354 A1    Oct. 11, 2012

(30) Foreign Application Priority Data
Sep. 21, 2009    (FR) .................................. 09 56477

(51) Int. Cl.
*G01N 33/68*    (2006.01)
(52) U.S. Cl.
CPC ................. *G01N 33/6872* (2013.01)
(58) Field of Classification Search
CPC ............. G01N 33/6872; G01N 33/9486; G01N 2500/00
USPC ........................................................ 424/9.2
See application file for complete search history.

(56) References Cited

U.S. PATENT DOCUMENTS

| 3,665,016 A * | 5/1972 | Bourdais ...................... 544/373 |
| 5,331,008 A * | 7/1994 | Duhamel et al. ............. 514/513 |
| 5,919,473 A * | 7/1999 | Elkhoury ...................... 424/422 |
| 7,112,403 B1 | 9/2006 | Patel et al. |
| 2006/0110792 A1 * | 5/2006 | Pausch et al. ............... 435/69.1 |
| 2011/0142940 A1 * | 6/2011 | Leguen et al. ................ 424/489 |

OTHER PUBLICATIONS

MacDonald et al, J. Pharm. & Pharmacol. 1(1):569-575, 1949.*
Xing et al, Anesth. & Analg. 97:1020-1024, 2003.*
Bensimon et al, J. Neurol. 249:609-615, 2002.*
Ling et al, J. Pharmacol. and Exp. Therap. 232(1):149-155, 1985.*
Houghten et al, J. Comb. Chem. 10:3-19, 2008; available online Dec. 8, 2007.*
Mahan et al, J. Am Podiatr. Med. Assoc. 83(11):607-614, 1993; abstract only.*
Provinciali et al, Int. J. Immunopharmacol. 18(10):577-586, 1996; abstract only.*
Heurteaux et al, EMBO J. 23:2684-2695, 2004).*
Alloui et al, The EMBO J. 25:2368-2376, 2006.*
Lee, J. Pharmacology and Experimental Therapeutics 75(2):161-173, 1942.*
Stasiak et al, Contemporary Topics in Laboratory Animal Science 42(4):13-20, 2003.*
International Search Report for PCT/FR2010/051968.
Alloui Abdelkrim et al: "TREK-1, a K+ channel involved in polymodal pain perception", EMBO Journal, Oxford University Press, Surrey, GB LNKD DOI:10.1038/SJ.EMBOJ.7601116, vol. 25, No. 11, (Jun. 1, 2006), pp. 2368-2376.
Alloui A et al: "The TREK-1 channel: An attractive target for the development of new analgesics?", Douleur Et Analgesie 200811 FR LNKD-DOI:10.1007/S11724-008-0108-1, vol. 21, No. 4, (Nov. 2008), pp. 215-220.
Duprat F et al: "The neuroprotective agent riluzole activates the two P domain K+ channels TREK-1 and TRAAK", Molecular Pharmacology, American Society for Pharmacology and Experimental Therapeutics, US, vol. 57, No. 5, (May 1, 2000), pp. 906-912.
Noel Jacques et al: "The mechano-activated K+ channels TRAAK and TREK-1 control both warm and cold perception.", The EMBO Journal May 6, 2009 LNKD-Pubmed:19279663, vol. 28, No. 9, (May 6, 2009), pp. 1308-1318.
Durieux et al: "Prevalence and management of pain in a hospital: a cross-sectional study", Mar. 31, 2001, pp. 572-576, vol. 30, No. 12, Presse Med.
Breivik et al, "Survey of chronic pain in Europe: prevalence, impact on daily life, and treatment", May 2006, pp. 287-333, vol. 10, No. 4, Eur. J. Pain.
Jow et al, "Validation of a Medium-Throughput Electrophysiological Assay for KCNQ2/3 Channel Enhancers Using IonWorks HT", 2007, pp. 1059-1067, vol. 12, No. 8, Journal of Biomolecular Screening.
Matthes et al, "Activity of the δ-Opioid Receptor is Partically Reduced, Whereas Activity of the κ-Receptor is Maintained in Mice Lacking the μ-Receptor", Sep. 15, 1998, pp. 7285-7295, vol. 18, No. 18, The Journal of Neuroscience.
Takahira et al, "Fenamates and diltiazem modulate lipid-sensititve mechano-gated 2P domain K+ channels", 2005, pp. 474-478, vol. 451, Pflugers Arch—Eur J. Physiol.
Romberg et al, "Comparison of morphine-6-glucuronide and morphine on respiratory depressant and antinociceptive responses in wild type and μ-opioid receptor deficient mice", 2003, pp. 862,70, vol. 91, No. 6, British Journal of Anaesthesia.
Danthi et al, "Caffeic Acid Esters Activate TREK-1 Potassium Channels and Inhibit Depolarization-Dependent Secretion", 2004, pp. 599-610, vol. 65, No. 3, Molecular Pharmacology.
Fink et al, "A neuronal two P domain K+ channel stimulated by arachidonic acid and polyunsaturated fatty acids", 1998, pp. 3297-3308, vol. 17, No. 12, The EMBO Journal.
Falconer et al, "High-Throughput Screening for Ion Channel Modulators", 2002, pp. 460-465, vol. 7, No. 5, Journal of Biomolecular Screening.

(Continued)

*Primary Examiner* — Kevin Hill
(74) *Attorney, Agent, or Firm* — Stephen J. Weyer, Esq.; Stites & Harbison. PLLC.

(57) ABSTRACT

The present invention relates to treating and preventing pain. More particularly the present invention demonstrates the involvement of K2P potassium channels in the antalgic effect of morphine. The present invention therefore provides a screening method for identifying antalgics.

4 Claims, 4 Drawing Sheets

(56) References Cited

OTHER PUBLICATIONS

Dahan et al, "Anesthetic Potency and Influence of Morphine and Sevoflurane on Respiration in μ-Opioid Receptor Knockout Mice", 2001, pp. 824-832, vol. 94, Anesthesiology.

Zuo et al, "The Role of Opioid Receptor Internalization and β-Arrestins in the Development of Opioid Tolerance", 2005, pp. 728-734, vol. 101, Anesth. Analg.

Roy et al, "μ-Opioid receptor-knockout mice: the role of μ-opioid receptor in gastrointestinal transit", 1998, pp. 281-283, vol. 56, Molecular Brain Research.

Ocana et al, "Potassium channels and pain: present realitites and future opportunities", 2004, pp. 203-219, vol. 500, European Journal of Pharmacology.

Basbaum et al, "Pain",1999, pp. R429-431, vol. 9, No. 12, Current Biology.

\* cited by examiner

SEQUENCE LISTING

```
<160> NUMBER OF SEQ ID NOS: 3

<210> SEQ ID NO 1
<211> LENGTH: 426
<212> TYPE: PRT
<213> ORGANISM: Homo sapiens
<220> FEATURE:
<221> NAME/KEY: VARSPLIC
<222> LOCATION: (1)..(16)
<223> OTHER INFORMATION: MLPSASRERPGYRAGV -> MMNPRAKRDFYL (in isoform 3)
<220> FEATURE:
<221> NAME/KEY: VARSPLIC
<222> LOCATION: (2)..(16)
<223> OTHER INFORMATION: Missing (in isoform 2)

<400> SEQUENCE: 1

Met Leu Pro Ser Ala Ser Arg Glu Arg Pro Gly Tyr Arg Ala Gly Val
1               5                   10                  15

Ala Ala Pro Asp Leu Leu Asp Pro Lys Ser Ala Ala Gln Asn Ser Lys
            20                  25                  30
```

```
Pro Arg Leu Ser Phe Ser Thr Lys Pro Thr Val Leu Ala Ser Arg Val
             35                  40                  45

Glu Ser Asp Thr Thr Ile Asn Val Met Lys Trp Lys Thr Val Ser Thr
 50                  55                  60

Ile Phe Leu Val Val Leu Tyr Leu Ile Gly Ala Thr Val Phe
 65                  70                  75                  80

Lys Ala Leu Glu Gln Pro His Glu Ile Ser Gln Arg Thr Thr Ile Val
                 85                  90                  95

Ile Gln Lys Gln Thr Phe Ile Ser Gln His Ser Cys Val Asn Ser Thr
            100                 105                 110

Glu Leu Asp Glu Leu Ile Gln Gln Ile Val Ala Ala Ile Asn Ala Gly
            115                 120                 125

Ile Ile Pro Leu Gly Asn Thr Ser Asn Gln Ile Ser His Trp Asp Leu
            130                 135                 140

Gly Ser Ser Phe Phe Phe Ala Gly Thr Val Ile Thr Thr Ile Gly Phe
145                 150                 155                 160

Gly Asn Ile Ser Pro Arg Thr Glu Gly Gly Lys Ile Phe Cys Ile Ile
                165                 170                 175

Tyr Ala Leu Leu Gly Ile Pro Leu Phe Gly Phe Leu Leu Ala Gly Val
            180                 185                 190

Gly Asp Gln Leu Gly Thr Ile Phe Gly Lys Gly Ile Ala Lys Val Glu
            195                 200                 205

Asp Thr Phe Ile Lys Trp Asn Val Ser Gln Thr Lys Ile Arg Ile Ile
            210                 215                 220

Ser Thr Ile Ile Phe Ile Leu Phe Gly Cys Val Leu Phe Val Ala Leu
225                 230                 235                 240

Pro Ala Ile Ile Phe Lys His Ile Glu Gly Trp Ser Ala Leu Asp Ala
                245                 250                 255

Ile Tyr Phe Val Val Ile Thr Leu Thr Thr Ile Gly Phe Gly Asp Tyr
            260                 265                 270

Val Ala Gly Gly Ser Asp Ile Glu Tyr Leu Asp Phe Tyr Lys Pro Val
            275                 280                 285

Val Trp Phe Trp Ile Leu Val Gly Leu Ala Tyr Phe Ala Ala Val Leu
            290                 295                 300

Ser Met Ile Gly Asp Trp Leu Arg Val Ile Ser Lys Thr Lys Glu
305                 310                 315                 320

Glu Val Gly Glu Phe Arg Ala His Ala Ala Glu Trp Thr Ala Asn Val
                325                 330                 335

Thr Ala Glu Phe Lys Glu Thr Arg Arg Arg Leu Ser Val Glu Ile Tyr
            340                 345                 350

Asp Lys Phe Gln Arg Ala Thr Ser Ile Lys Arg Lys Leu Ser Ala Glu
            355                 360                 365

Leu Ala Gly Asn His Asn Gln Glu Leu Thr Pro Cys Arg Arg Thr Leu
            370                 375                 380

Ser Val Asn His Leu Thr Ser Glu Arg Asp Val Leu Pro Pro Leu Leu
385                 390                 395                 400

Lys Thr Glu Ser Ile Tyr Leu Asn Gly Leu Thr Pro His Cys Ala Gly
                405                 410                 415

Glu Glu Ile Ala Val Ile Glu Asn Ile Lys
            420                 425

<210> SEQ ID NO 2
<211> LENGTH: 538
<212> TYPE: PRT
```

```
<213> ORGANISM: Homo sapiens
<220> FEATURE:
<221> NAME/KEY: VARSPLIC
<222> LOCATION: (1)..(12)
<223> OTHER INFORMATION: MFFLYTDFFLSL -> MKGDRTEGCRSDS (in isoform B)
<220> FEATURE:
<221> NAME/KEY: VARSPLIC
<222> LOCATION: (1)..(12)
<223> OTHER INFORMATION: MFFLYTDFFLSL -> MKFPIETPRKQVNWDPK (in
      isoform C)
<220> FEATURE:
<221> NAME/KEY: VARIANT
<222> LOCATION: (512)..(512)
<223> OTHER INFORMATION: A to T substitution

<400> SEQUENCE: 2
```

Met Phe Phe Leu Tyr Thr Asp Phe Phe Leu Ser Leu Val Ala Val Pro
1               5                   10                  15

Ala Ala Ala Pro Val Cys Gln Pro Lys Ser Ala Thr Asn Gly Gln Pro
            20                  25                  30

Pro Ala Pro Ala Pro Thr Pro Thr Pro Arg Leu Ser Ile Ser Ser Arg
            35                  40                  45

Ala Thr Val Val Ala Arg Met Glu Gly Thr Ser Gln Gly Gly Leu Gln
50                  55                  60

Thr Val Met Lys Trp Lys Thr Val Ala Ile Phe Val Val Val Val Val
65                  70                  75                  80

Val Tyr Leu Val Thr Gly Gly Leu Val Phe Arg Ala Leu Glu Gln Pro
                85                  90                  95

Phe Glu Ser Ser Gln Lys Asn Thr Ile Ala Leu Glu Lys Ala Glu Phe
                100                 105                 110

Leu Arg Asp His Val Cys Val Ser Pro Gln Glu Leu Glu Thr Leu Ile
            115                 120                 125

Gln His Ala Leu Asp Ala Asp Asn Ala Gly Val Ser Pro Ile Gly Asn
            130                 135                 140

Ser Ser Asn Asn Ser Ser His Trp Asp Leu Gly Ser Ala Phe Phe Phe
145                 150                 155                 160

Ala Gly Thr Val Ile Thr Thr Ile Gly Tyr Gly Asn Ile Ala Pro Ser
                165                 170                 175

Thr Glu Gly Gly Lys Ile Phe Cys Ile Leu Tyr Ala Ile Phe Gly Ile
                180                 185                 190

Pro Leu Phe Gly Phe Leu Leu Ala Gly Ile Gly Asp Gln Leu Gly Thr
            195                 200                 205

Ile Phe Gly Lys Ser Ile Ala Arg Val Glu Lys Val Phe Arg Lys Lys
210                 215                 220

Gln Val Ser Gln Thr Lys Ile Arg Val Ile Ser Thr Ile Leu Phe Ile
225                 230                 235                 240

Leu Ala Gly Cys Ile Val Phe Val Thr Ile Pro Ala Val Ile Phe Lys
                245                 250                 255

Tyr Ile Glu Gly Trp Thr Ala Leu Glu Ser Ile Tyr Phe Val Val Val
                260                 265                 270

Thr Leu Thr Thr Val Gly Phe Gly Asp Phe Val Ala Gly Gly Asn Ala
            275                 280                 285

Gly Ile Asn Tyr Arg Glu Trp Tyr Lys Pro Leu Val Trp Phe Trp Ile
290                 295                 300

Leu Val Gly Leu Ala Tyr Phe Ala Ala Val Leu Ser Met Ile Gly Asp
305                 310                 315                 320

Trp Leu Arg Val Leu Ser Lys Lys Thr Lys Glu Glu Val Gly Glu Ile
                325                 330                 335

```
Lys Ala His Ala Ala Glu Trp Lys Ala Asn Val Thr Ala Glu Phe Arg
            340                 345                 350

Glu Thr Arg Arg Arg Leu Ser Val Glu Ile His Asp Lys Leu Gln Arg
        355                 360                 365

Ala Ala Thr Ile Arg Ser Met Glu Arg Arg Leu Gly Leu Asp Gln
370                 375                 380

Arg Ala His Ser Leu Asp Met Leu Ser Pro Glu Lys Arg Ser Val Phe
385                 390                 395                 400

Ala Ala Leu Asp Thr Gly Arg Phe Lys Ala Ser Ser Gln Glu Ser Ile
                405                 410                 415

Asn Asn Arg Pro Asn Asn Leu Arg Leu Lys Gly Pro Glu Gln Leu Asn
            420                 425                 430

Lys His Gly Gln Gly Ala Ser Glu Asp Asn Ile Ile Asn Lys Phe Gly
        435                 440                 445

Ser Thr Ser Arg Leu Thr Lys Arg Lys Asn Lys Asp Leu Lys Lys Thr
    450                 455                 460

Leu Pro Glu Asp Val Gln Lys Ile Tyr Lys Thr Phe Arg Asn Tyr Ser
465                 470                 475                 480

Leu Asp Glu Glu Lys Lys Glu Glu Thr Glu Lys Met Cys Asn Ser
                485                 490                 495

Asp Asn Ser Ser Thr Ala Met Leu Thr Asp Cys Ile Gln Gln His Ala
            500                 505                 510

Glu Leu Glu Asn Gly Met Ile Pro Thr Asp Thr Lys Asp Arg Glu Pro
        515                 520                 525

Glu Asn Asn Ser Leu Leu Glu Asp Arg Asn
    530                 535

<210> SEQ ID NO 3
<211> LENGTH: 393
<212> TYPE: PRT
<213> ORGANISM: Homo sapiens
<220> FEATURE:
<221> NAME/KEY: VARSPLIC
<222> LOCATION: (1)..(1)
<223> OTHER INFORMATION: M -> MTTAPQEPPARPLQAGSGAG PAPGRAM (in
      isoform 2)
<220> FEATURE:
<221> NAME/KEY: VARIANT
<222> LOCATION: (328)..(328)
<223> OTHER INFORMATION: P to L substitution

<400> SEQUENCE: 3

Met Arg Ser Thr Thr Leu Leu Ala Leu Ala Leu Val Leu Leu Tyr
1               5                   10                  15

Leu Val Ser Gly Ala Leu Val Phe Arg Ala Leu Glu Gln Pro His Glu
                20                  25                  30

Gln Gln Ala Gln Arg Glu Leu Gly Glu Val Arg Glu Lys Phe Leu Arg
        35                  40                  45

Ala His Pro Cys Val Ser Asp Gln Glu Leu Gly Leu Leu Ile Lys Glu
    50                  55                  60

Val Ala Asp Ala Leu Gly Gly Gly Ala Asp Pro Glu Thr Asn Ser Thr
65                  70                  75                  80

Ser Asn Ser Ser His Ser Ala Trp Asp Leu Gly Ser Ala Phe Phe Phe
                85                  90                  95

Ser Gly Thr Ile Ile Thr Thr Ile Gly Tyr Gly Asn Val Ala Leu Arg
            100                 105                 110

Thr Asp Ala Gly Arg Leu Phe Cys Ile Phe Tyr Ala Leu Val Gly Ile
```

-continued

```
            115                 120                 125
Pro Leu Phe Gly Ile Leu Leu Ala Gly Val Gly Asp Arg Leu Gly Ser
        130                 135                 140
Ser Leu Arg His Gly Ile Gly His Ile Glu Ala Ile Phe Leu Lys Trp
145                 150                 155                 160
His Val Pro Pro Glu Leu Val Arg Val Leu Ser Ala Met Leu Phe Leu
                165                 170                 175
Leu Ile Gly Cys Leu Leu Phe Val Leu Thr Pro Thr Phe Val Phe Cys
            180                 185                 190
Tyr Met Glu Asp Trp Ser Lys Leu Glu Ala Ile Tyr Phe Val Ile Val
        195                 200                 205
Thr Leu Thr Thr Val Gly Phe Gly Asp Tyr Val Ala Gly Ala Asp Pro
    210                 215                 220
Arg Gln Asp Ser Pro Ala Tyr Gln Pro Leu Val Trp Phe Trp Ile Leu
225                 230                 235                 240
Leu Gly Leu Ala Tyr Phe Ala Ser Val Leu Thr Thr Ile Gly Asn Trp
                245                 250                 255
Leu Arg Val Val Ser Arg Arg Thr Arg Ala Glu Met Gly Gly Leu Thr
            260                 265                 270
Ala Gln Ala Ala Ser Trp Thr Gly Thr Val Thr Ala Arg Val Thr Gln
        275                 280                 285
Arg Ala Gly Pro Ala Ala Pro Pro Glu Lys Glu Gln Pro Leu Leu
    290                 295                 300
Pro Pro Pro Pro Cys Pro Ala Gln Pro Leu Gly Arg Pro Arg Ser Pro
305                 310                 315                 320
Ser Pro Pro Glu Lys Ala Gln Pro Pro Ser Pro Pro Thr Ala Ser Ala
                325                 330                 335
Leu Asp Tyr Pro Ser Glu Asn Leu Ala Phe Ile Asp Glu Ser Ser Asp
                340                 345                 350
Thr Gln Ser Glu Arg Gly Cys Pro Leu Pro Arg Ala Pro Arg Gly Arg
        355                 360                 365
Arg Arg Pro Asn Pro Pro Arg Lys Pro Val Arg Pro Arg Gly Pro Gly
    370                 375                 380
Arg Pro Arg Asp Lys Gly Val Pro Val
385                 390
```

USE OF K2P POTASSIUM CHANNEL ACTIVATORS AS ANTALGICS

The present invention relates to treating and preventing pain. More particularly, the present invention demonstrates the involvement of K2P potassium channels in the antalgic effect of morphine. The present invention therefore provides a screening method for identifying antalgics.

Pain may be defined as an unpleasant sensorial and emotional experience related to an existing or potential tissue lesion or described in terms of such a lesion. Practically, management of pain perceived by the patient results from the interaction between the pain generating phenomenon, the individual's capabilities of integrating it and the response of professionals in a situation for recognizing it and treating it.

At least 50% of adult in-patients suffer from pain (Durieux et al., 2001 Presse Med. 30:572-6). The intensity of post-operative pain may be a risk factor of persistence of pain beyond this period (Basbaum et al., 1999 Curr Biol. 9:R429-31) and its efficient control is associated with reduction of post-operative complications. Stubborn chronic pains are a source of major alterations in the quality of life, disablement and handicaps. They induce a significant consumption of treatments as well as many work stoppages. In a large European survey, one fifth of the subjects interviewed by telephone stated that they were suffering from chronic pains, among which 85% of them pointed out that they had consulted at least once a physician during the last six months. Thus, in his/her daily practice, every physician is confronted with such patients and this number will increase considering the ageing of the population. Pain is also the most frequent symptom related to cancer. It concerns 30 to 50% of cancer patients, including all stages, and 65 to 90% of patients at an advanced stage. The very large majority of interviewed patients suffering from chronic pains pointed out that they were receiving an antalgic drug treatment. Prescription drugs which are the most often mentioned are anti-inflammatories and weak opioids, while strong opioids are mentioned with a frequency of the order of 5%. As regards over-the-counter drugs, the mentioned drugs are anti-inflammatories and paracetamol, and to a lesser extent, weak opioids in countries where they may be obtained without any prescription (Breivik et al., 2006 Eur J Pain. 10:287-333).

Drug management of pain remains a problem with drugs for which the benefit/risk ratios, depending on the patients (individual sensitiveness to treatments, elderly subjects, children, etc.), are not always in favor of beneficial effects. Therapeutic innovations are not frequent and old products are still used as first line products in many indications.

Opioid antalgics group morphine and the whole of the hemi-synthetic or synthetic derivatives of this alkaloid. Morphine remains the reference product in the treatment of pain with intense nociception excesses, notably post-operative pain and cancer pain. Opioids have antalgic effects but also psychodysleptic, respiratory depressive, emetic, cardiovascular effects on smooth muscles and on the immune system. The undesirable effects related to the use of opioids are characterized by almost systematic constipation, nauseas and vomiting in more than half of the patients, frequent sedation, the risk of respiratory depression requiring supervision, and hallucinations or confusion in elderly subjects which although rare require reduction in the doses. Further the constipating effects are a major handicap in particular in elderly persons and in cancer treatment.

Morphine produces its effects via activation of opioid receptors, of which three sub-types (μ, δ and κ) are known. The therapeutic (analgesic and undesirable) effects (for example constipation and respiratory depression) preferentially involve the activation of the μ receptor (Roy et al., 1998 Brain Res Mol Brain Res. 56:281-3). The desire to dissociate these effects therefore imposes work downstream from this receptor. Although the exact mechanism of action is not known, the connection of morphine with the μ receptor causes activation of $Gi_{/O}$ proteins, inhibition of adenylate cyclase, activation of phospholipase C, and consequently inhibition of voltage-dependent calcium channels as well as activation of potassium channels (Zuo, 2005 Anesth. Analg. 101:728-34). Among the potassium channels, two inward rectification channels, the GIRK channels and the channels depending on ATP ($K_{ATP}$), were described as being partly involved in the antalgic effect of morphine (Ocaña et al., 2004 Eur J Pharmacol. 500:203-19). However, potential involvement of other potassium channels, such as the K2P potassium channels in the antalgic effect of morphine has not been described to this day.

In order to overcome the undesirable effects of morphine, the pharmaceutical industry is presently either developing opioid antalgics without any action on the μ receptors, or peripheral antagonists of the μ receptors which however are only opposed to the constipating effects, and not to the respiratory depressive effects. However, the first ones risk having lesser antalgic efficiency than that of agonists of μ receptors, and the second ones have to be jointly prescribed with the opioids.

It would therefore be desirable to obtain an antalgic as efficient as morphine, but without constipating and respiratory depressive effects, two major undesirable effects in terms of frequency and seriousness respectively.

DESCRIPTION OF THE INVENTION

The present invention for the first time demonstrates the involvement of K2P potassium channels and more particularly of TREK-1 and TRAAK, in the antalgic effect of morphine. Thus, deletion of the gene coding for TREK-1 or TRAAK leads to the suppression of the antalgic effect of the opiate. Moreover, deletion of the gene coding for TREK-1 or TRAAK does not reduce the constipating and/or respiratory depressive effect of morphine. The TREK-1 and TRAAK channels are therefore required for the antalgic action but do not participate in these undesirable effects. The K2P potassium channels of the TREK/TRAAK family may therefore be used as targets for screening new antalgics which are as efficient as morphine with a better benefit/risk ratio.

The present invention therefore provides a screening method for isolating novel efficient and well tolerated antalgics and therefore allows syntheses, validation, development and formulation of the thereby selected antalgics.

The Use of K2P Potassium Channels as Targets

The TREK-1 and TRAAK potassium channels are involved in the antalgic effect of morphine but not in its undesirable effects, the K2P potassium channels of the TREK/TRAAK family are useful as targets during screenings for identifying antalgic compounds. The thereby identified antalgic compounds are characterized in that they do not have any constipating and/or respiratory depressive effect.

The invention therefore relates to a screening method for identifying an antalgic compound, comprising the following steps:

a) identifying an activator of a K2P potassium channel by screening candidate compounds;
b) measuring the antalgic effect of said activator; and optionally,
c) measuring the constipating and/or respiratory depressive effect of said activator.

The method according to the invention may include the additional step of selecting an antalgic compound without any constipating and/or respiratory depressive effect.

By <<antalgic compound >>, is meant here a compound capable of attenuating or abolishing pain.

By <<K2P potassium channel >>, is meant here the UniProt No. TC 1.A.1.8 family (also called <<two pore domain potassium channel family>>). Preferably the K2P potassium channel according to the invention is selected from the members of the TREK/TRAAK family, more particularly from TREK-1, TREK-2 and TRAAK.

By <<TREK-1 channel >> is meant here a K2P potassium channel comprising at least one sub-unit, the sequence of which is shown in the entry: Swiss-Prot No. 95069 (SEQ ID NO: 1) or the sequence of which is derived from this sequence. Preferably, the TREK-1 channel is a channel consisting of two sub-units with sequences selected from the sequence SEQ ID NO: 1 and its derived sequences. The TREK-1 channel may for example be a homodimeric channel consisting of two sub-units of sequence SEQ ID NO: 1.

By <<TREK-2 channel >>, is meant here a K2P potassium channel comprising at least one sub-unit, the sequence of which is shown in the entry: Swiss-Prot No. P57789 (SEQ ID NO: 2) or the sequence of which is derived from this sequence. Preferably the TREK-2 channel is a channel consisting of two sub-units with sequences selected from the sequence SEQ ID NO: 2 and its derived sequences. The TREK-2 channel may for example be a homodimeric channel consisting of two sub-units with sequence SEQ ID NO: 2.

By <<TRAAK channel >>, is meant here a K2P potassium channel comprising at least one sub-unit, the sequence of which is shown in the entry: Swiss-Prot No. Q9NYG8 (SEQ ID NO: 3) or the sequence of which is derived from the latter sequence. Preferably, the TRAAK channel is a channel consisting of two sub-units with sequences selected from SEQ ID NO: 3 and its derived sequences. The TRAAK channel may for example be a homodimeric channel consisting of two sub-units with sequence SEQ ID NO: 3.

The <<derived sequences>> notably include splicing variants, allelic variants and homolog sequences in non-human mammal species. The derived sequences notably include sequences at least 50, 60, 70, 80, 85, 90, 95 or 99% identical with one of the sequences SEQ ID NO: 1, SEQ ID NO: 2 or SEQ ID NO: 3.

By <<a sequence of amino acids at least 95% (for example) identical with a reference sequence>>, is meant a sequence identical with the reference sequence except that this sequence may include up to five mutations (substitutions, deletions and/or insertions) for each portion of one hundred amino acids of the reference sequence. Thus for a reference sequence of a 100 amino acids, a fragment of 95 amino acids and a sequence of a 100 amino acids including 5 substitutions relatively to the reference sequence are two examples of sequences 95% identical with the reference sequence. The identity percentage is generally determined by using a software package for analyzing sequences. The amino acid sequences to be compared are aligned in order to obtain the identity degree maximum. For this purpose, it may be necessary to artificially introduce spaces (gaps) in the sequence. Once optimum alignment is achieved, the identity degree is established by recording all the positions for which the amino acids of both compared sequences are identical, relatively to the total number of positions. The program <<needle>>, which resorts to the global alignment Needleman-Wunsch algorithm for finding the optimum alignments (with gaps) of two sequences over the whole of their length, may for example be used. This program is notably available on the ebi.ac.uk web site.

The derived sequences may differ from the reference sequence by substitution, deletion and/or insertion of one or more amino acids, and this in position such that these modifications do not significantly affect the biological activity of the peptides. The substitutions may notably correspond to conservative substitutions.

In a particular embodiment, the sequence of the derivatives differs from the sequences SEQ ID NOS: 1, 2 or 3 only by the presence of conservative substitutions. Conservative substitutions are substitutions of amino acids of the same class, such as substitutions of amino acids with non-charged side chains (such as asparagine, glutamine, serine, cysteine and tyrosine), of amino acids with basic side chains (such as lysine, arginine and histidine), of amino acids with acid side chains (such as aspartic and glutamic acid), of amino acids with apolar side chains (such as alanine, valine, leucine, isoleucine, proline, phenylalanine, methionine and tryptophan).

By <<activator of a K2P potassium channel>>, is meant here a compound capable of increasing the biological activity of a K2P potassium channel. Unlike morphine, the activators according to the invention do not have the effect of activating opioid receptors. Consequently, they are without any constipating and/or respiratory depressive effect. Preferably, the activators directly act on the K2P potassium channel, i.e. they interact directly with said channel. The activators may also activate the K2P potassium channel via a signaling cascade. In the second case, the activators necessarily act downstream from the opioid receptors, i.e. they modulate the activity of a component of the cascade which is located upstream from the K2P potassium channel, but downstream from the opioid receptors. The fact that an activator of the K2P potassium channel acts downstream from the opioid receptors may easily be tested by comparing the activity of the K2P potassium channel in the presence and in the absence of an inhibitor of opioid receptors such as for example naloxone. The fact that the activity of the K2P potassium channel is the same in the presence and in the absence of the inhibitor of opioid receptors indicates that the activator acts downstream from the opioid receptors.

Methods for determining whether a compound is capable of increasing the biological activity of a K2P potassium channel are well known to one skilled in the art.

For example it is possible to identify an activator of a TREK-1 channel by using the method described by Alloui et al. (EMBO J. 2006 25:2368-76). Such a method may for example comprise the following steps:
providing a cell expressing a TREK-1 channel (for example a DRG neuron);
measuring the current in the absence of the candidate compound; and
measuring the current in the presence of the candidate compound;
where an increase in the current in the presence of the candidate compound indicates that the candidate compound is an activator of the TREK-1 channel. Said current may for example be induced by a compound such as arachidonic acid or by intracellular acidification. More particularly the activators of the TREK-1 channel are capable of producing an increase in the intensity of the current from dorsal root ganglia neurons of wild mice where the intensity of the current is evaluated by the so-called <<patch-clamp >> technique under entire cell conditions, under the conditions described in Alloui et al. (EMBO J. 2006 25:2368-76).

It is also possible to identify an activator of a TREK-1 channel by using the method described by Duprat et al. (Mol. Pharmacol. 2000, 57:906-912). In this method, heterologous expression systems (for example COS cells) are transfected with the gene coding for TREK-1, and the currents are then measured by the <<patch-clamp>> technique under entire cell conditions.

The methods described in Alloui et al. (EMBO J. 2006 25:2368-76) and in Duprat et al. (Mol. Pharmacol. 2000, 57 :906-912) are also applicable to the study of K2P potassium channels other than TREK-1, by replacing invalidated animals for TREK-1 with invalidated animals for the channel which is desirably studied (for example TREK-2 or TRAAK).

Alternatively, the screening method may be applied by using a high throughput screening platform adapted to the screening of potassium channel modulators (Falconer et al., 2002 J Biomol Screen. 7:460-5; Ford et al., 2002 Prog Drug Res. 58:133-68).

The thereby identified antalgic compounds are characterized in that they do not have any constipating and/or respiratory depressive effect. Moreover, they may also be without any other undesirable effects.

By a compound having an <<antalgic effect>>, is meant here a compound capable of attenuating or abolishing pain. The antalgic effect of a compound may be measured by any method well known to one skilled in the art, for example by the mechanical sensitivity test of von Frey or by the thermal test of immersion of the tail in hot water (see Examples 1 and 2).

By a compound having a <<constipating effect>>, is meant here a compound capable of reducing defecation. The constipating effect of a compound may be measured by any method well known to one skilled in the art, for example by using a global method for collecting feces (see Examples 1 and 4).

By a compound having a <<respiratory depressive effect>>, is meant here a compound capable of decreasing respiratory (or breathing) frequency. The respiratory depressive effect of a compound may be measured by any method well known to one skilled in the art, for example by measuring the breathing frequency by means of a barometric plethysmograph (see Examples 1 and 5).

By a compound <<without any constipating and/or respiratory depressive effect>>, is meant a compound in the presence of which defecation and/or breathing frequency is greater than or equal to 70%, 80%, 90% or 95% of the observed value in the absence of said compound. Preferably, defecation and/or breathing frequency is not reduced in a statistically significant way in the presence of said compound. As the constipating and/or respiratory depressive effects are dose-dependent, the absence of a constipating and/or respiratory depressive effect of an antalgic compound is preferably evaluated at an equianalgesic dose to that at which morphine produces an antalgic effect.

Within the scope of the screening methods, the candidate compounds may for example correspond to natural ligands of a K2P potassium channel, to chemical molecules, to aptamers, peptides and antibodies. In a preferred embodiment, the candidate compounds are small chemical molecules (small molecules).

In a particular embodiment, the invention aims at a screening method for identifying an antalgic compound comprising the following steps:
 a) providing a candidate compound;
 b) determining whether said candidate compound activates a K2P potassium channel;
 where the determination that said candidate compound activates said K2P potassium channel indicates that said candidate compound is an antalgic compound.

This method may further comprise the step of measuring the antalgic effect of said candidate compound which activates said K2P potassium channel, and/or the step for measuring the constipating and/or respiratory depressive effect of said compound activating said K2P potassium channel.

The method according to the invention may include the additional step of selecting an antalgic compound without any constipating and/or respiratory depressive effect.

The use of a K2P potassium channel as a target for identifying an antalgic compound upon screening candidate compounds is another object of the invention. More specifically, such a use aims at identifying activators of K2P potassium channels, which have an antalgic effect.

The screening method according to the invention may be conducted in vitro or in vivo. When these methods involve experiments on model animals such as rats or mice, these animals are sacrificed at the end of these methods. Thus, these methods may comprise an additional step for sacrificing the model animals which may have been used.

Therapeutic Use of K2P Potassium Channel Activators

Given that the invalidation of the channels TREK-1 and TRAAK leads to the decrease of the antalgic effects of morphine without affecting the undesirable effects such as the constipating and/or respiratory depressive effect, the activators of channels TREK-1 and TRAAK are antalgics without these undesirable effects of morphine. The invention therefore relates to an activator of a K2P potassium channel of the TREK/TRAAK family for a use in treating or preventing pain. Such activators are particularly advantageous for treating or preventing pain when they are without any constipating and/or respiratory depressive effect.

The pain may be of diverse natures. It may be acute or chronic. This may for example be post-operative pain, pain associated with a hyperalgic attack, pain associated with cancer, osteoarticular pain, visceral pain or neuropathic pain, said pain occurring at any period of life. In a preferred embodiment, this is chronic pain and more particularly a chronic painful syndrome such as fibromyalgia, syndrome of the irritable intestine, or a pain sine materia. In another preferred embodiment, this is an intestinal, stomach or lung pain, either related or not to cancer, such as pain associated with colorectal cancer, colon cancer, stomach cancer, ulcerative colitis, with chronic inflammatory bowel disease (designated by the acronym IBD), with irritable intestine, with lung cancer or asthma.

The pain may be treated at any stage. By <<treatment>>, is meant curative treatment (aiming at least alleviating, curbing or halting pain). By <<prevention>>, is meant a prophylactic treatment (aiming at reducing the risk of occurrence of pain).

The activators may for example correspond to natural ligands of a K2P potassium channel, to chemical molecules, to aptamers, to peptides or to antibodies.

The activator according to the invention may for example correspond to one of the K2P potassium channel activators already known in the art. Thus, the channels of the TREK/ TRAAK family are reversibly opened by lysophospholipids which have big polar heads (lysophosphatidylcholine, lysophosphatidylinositol) and by polyunsaturated fatty acids (linolenic acid, arachidonic acid) (Fink et al., 1998 EMBO J. 17:3297-308). Caffeic acid esters, notably cinnamyl 1-3, 4-dihydroxy-α-cyanocinnamate (CDC) and caffeic acid phenethyl ester (CAPE), increase the TREK-1 current on adreno-fascicular bovine cells (Danthi et al., 2004 Mol Pharmacol. 65:599-610). Finally, fenamates such as flufenamic acid, niflumic acid and mefenamic acid activate TREK-1, TREK-2 and TRAAK channels in heterologous expression systems (Takahira et al., 2005 Pflugers Arch. 451:474-8). The compounds specifically mentioned above are examples of activator according to the invention.

Consequently, the activator according to the invention may for example be selected from a lysophospholipid, a polyunsaturated fatty acid, an ester of caffeic acid or a fenamate.

Alternatively, the K2P potassium channel activators may be isolated by screening methods described above in the paragraph entitled <<The use of K2P potassium channels as targets>>.

The invention also relates to a method for manufacturing a drug containing an activator of a K2P potassium channel comprising the following steps:
a) producing said drug;
b) measuring the antalgic effect of said drug and optionally,
c) measuring the constipating and/or respiratory depressive effect of said drug.

Such a manufacturing method, which allows testing of the quality of different production batches, is useful during industrial production of drugs. More particularly, this method gives the possibility of making sure that a given drug batch containing an activator of a K2P potassium channel has an antalgic effect and does not have any constipating and/or respiratory depressive effect. In step (a), the drug may be produced by any method known to one skilled in the art. The production of such a drug typically comprises the synthesis of the activator of a K2P potassium channel, and then its formulation as a pharmaceutical product.

The drug according to the invention may be intended to be administered via any suitable route, for example an oral, sublingual, nasal, buccal, transdermal, intravenous, subcutaneous, intramuscular and/or rectal route. In a drug, the active ingredients (i.e. the activator according to the invention) is combined with a pharmaceutically acceptable carrier (i.e. any solvent, dispersion medium, absorption-retarding agent, etc., which does not produce any secondary reaction, for example an allergic reaction, in humans or animals). The pharmaceutically acceptable carriers are well known to one skilled in the art and include those described in <<Remington's Pharmaceutical Sciences>> (Mack Publishing Company, Easton, USA, 1985).

The invention also relates to a method for treating or preventing pain, comprising the administration of a therapeutically effective amount of an activator of a K2P potassium channel to an individual being in need thereof. The individual is preferably a mammal, more particularly a human. The effective therapeutic dose may easily be determined by one skilled in the art.

The invention further relates to the use of an activator of a K2P potassium channel for preparing a drug for treating or preventing pain.

The following examples and figures illustrate the invention without limiting the scope thereof.

DESCRIPTION OF THE SEQUENCES OF THE LISTING OF SEQUENCES

Figure 1:
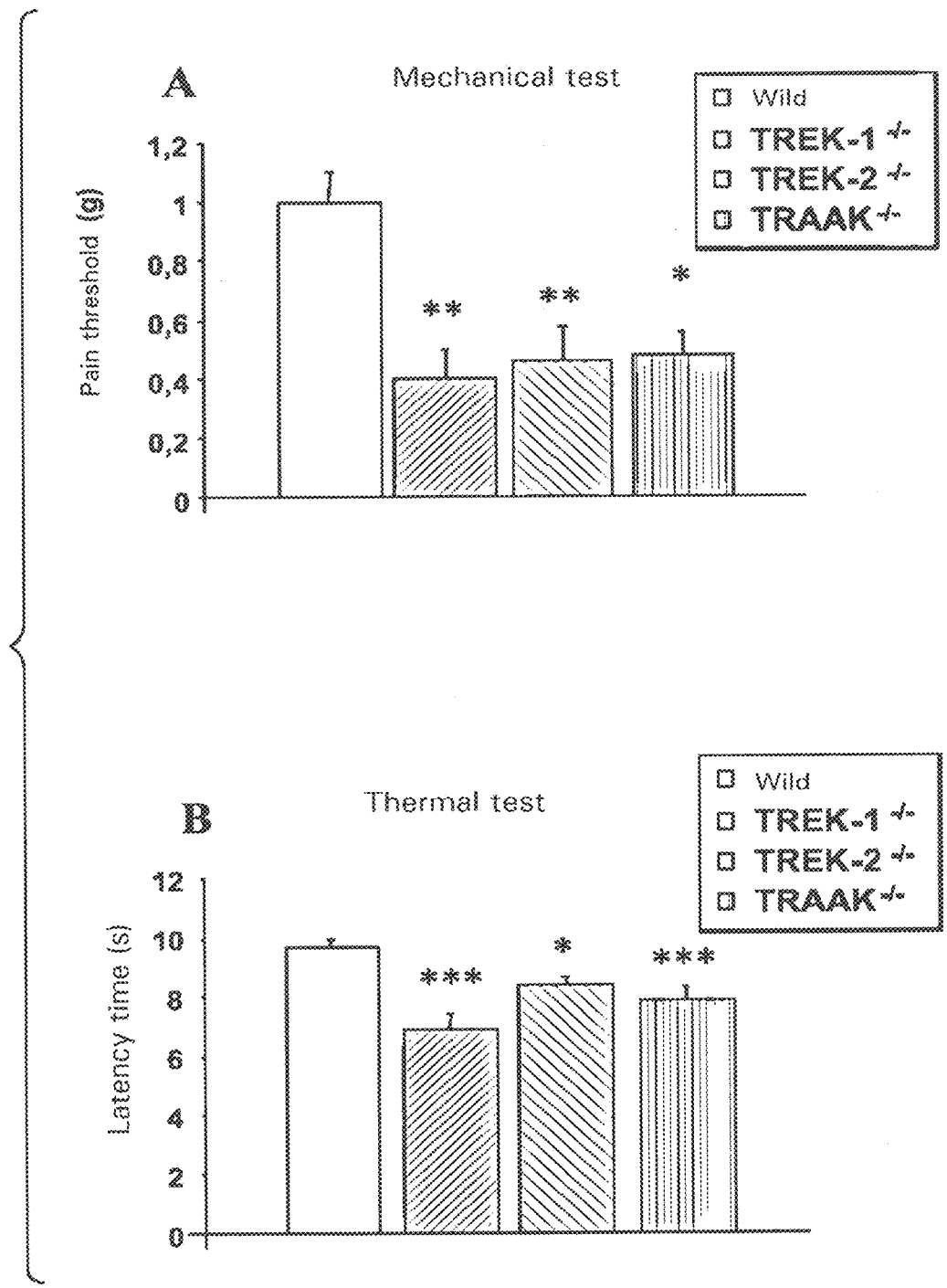
FIG. 1: In the basal state, the knock-out (KO) animals exhibit hypersensitivity to the mechanical test of von Frey (A) or to the thermal test (B) as compared with wild animals (WA) (WT vs. KO: Student's t test: *, P<0.05, , P<0.01, *, P<0.001, n=8/15 per group).

SEQ ID NO: 1 corresponds to the sequence of a sub-unit of a TREK-1 channel.
SEQ ID NO: 2 corresponds to the sequence of a sub-unit of a TREK-2 channel.
SEQ ID NO: 3 corresponds to the sequence of a sub-unit of a TRAAK channel.

EXAMPLES

Example 1

Procedures

Animals

Male mice C57BI/6J (Charles River Lab, France), TREK-1$^{-/-}$, TREK-2$^{-/-}$ and TRAAK$^{-/-}$ (IPMC, Nice-Sophia Antipolis), weighing from 20 to 30 grams were placed in a cage with food and water ad libitum in a thermoregulated environment at 22° C. with a day/night cycle of 12h/12 h. The details relating to the generation of KO animals were described earlier (Heurteaux et al., 2004 EMBO J. 23:2684-95; Guyon et al., 2009 J. Neurosc. 29:2528-33). The experiments were conducted as blind experiments in a calm room by the same experimenter while taking care in observing the regulatory requirements on animal experimentation.

Molecules

The following molecules were used: morphine hydrochloride (Cooper, Melun, France), naloxone hydrochloride (Sigma Chemical Co., St Louis, Mo.). The solutions were prepared extemporaneously in NaCl (0.9%). Naloxone (1 mg/kg, s.c.) was administered 15 minutes before injection of morphine or of carrier.

Nociception Tests

The tests used comprised tests using thermal stimuli (test of immersion of the tail in hot water at 46° C.) and mechanical stimuli (mechanical sensitivity in the test of filaments of von Frey). The thermal sensitivity is measured by the test of immersion of the tail in water at the nociceptive temperature of 46° C. (Janssen et al., 1963 Arzneimittelforschung. 13:502-7). The animal is held manually and the tail is immersed in a water-bath until withdrawal of the latter by the animal or until a <<cut-off>>, set to 30 s. The basal threshold (pre-treatment) is defined by the average of the first two latency times which do not differ by more than one second. The animals were accustomed to restraint for one week before the beginning of the experiment. The mechanical sensitivity is measured by applying filaments of von Frey (Bioseb) with increasing force (0.01 to 2 g) under the paws of the animal (Tal and Bennett, 1994 Pain. 57:375-82). The animals are placed in boxes (85×35 mm, opaque separation between the mice, a bottom with wire netting so as to access to the arch) 20 minutes before the test in order to accustom them to this. The filaments are pressed perpendicularly under the rear right paw of the mice until they are bent. This is operation is repeated five times, before passing to the next filament in the case when no reaction was obtained. When the exerted pressure corresponds to the tactile sensitivity threshold of the animal, the latter has a reaction of withdrawal of the paw equivalent to reflex kick. The pressure value of the filament is then retained as a threshold value.

Intestinal Transit

The evaluation of the intestinal transit was achieved by using an overall method for collecting feces in kinetics for 2 hours following injection of morphine or of carrier (NaCl 0.9%). The animals are placed in boxes (85×35 mm, opaque separation between the mice, bottom with wire netting for collecting feces), 20 minutes before the test, so as to become accustomed. The feces are collected and weighed immediately after collection, every hour for 2 hours following injection of morphine or of carrier.

Measurement of the Breathing Frequency

The breathing frequency was measured in a non-invasive way (Drorbaugh and Fenn, 1955 Pediatrics. 16:81-7; Matthes et al., 1998 J Neurosci. 18:7285-95) by using a barometric plethysmograph (Emka Technologies, VA, USA) including 8 rooms allowing parallel measurement on several animals. The software package 10× (Emka Technologies, VA, USA) was used for calculating the breathing frequency. Each dose of morphine or carrier was administered and their effects on the breathing frequency were evaluated in four wild mice and four TREK-1$^{-/-}$ mice in parallel. The animals were accustomed to the rooms for 15 mins before the injection. Analysis of the breathing frequency during this 15 minute period revealed stable breathing frequency. The average of the breathing frequency for this period was therefore used for normalizing the effect of morphine or of carrier on the breathing frequency for the duration of the test (90 minutes).

Statistical Analyses

The experimental data were analyzed by using the software package Sigma STAT, version 3.0 pour Windows (STAT32 Software Inc., San Diego, Calif.).

Example 2

Role of the TREK-1, TREK-2 and TRAAK Channels in the Physiology of Nociception

Regardless of the tests used, mechanical sensitivity test of von Frey (FIG. 1A) or thermal test of immersion of the tail in hot water at 46° C. (FIG. 1B), it was shown that TREK-1$^{-/-}$ or TRAAK$^{-/-}$ animals have significantly lower pain thresholds than wild animals. It was also shown that the pain thresholds of TREK-2$^{-/-}$ animals are significantly lower than those of wild animals (FIGS. 1A and 1B).

Example 3

Role of the TREK-1 Channels in the Antalgic Action of Morphine

Figure 2:
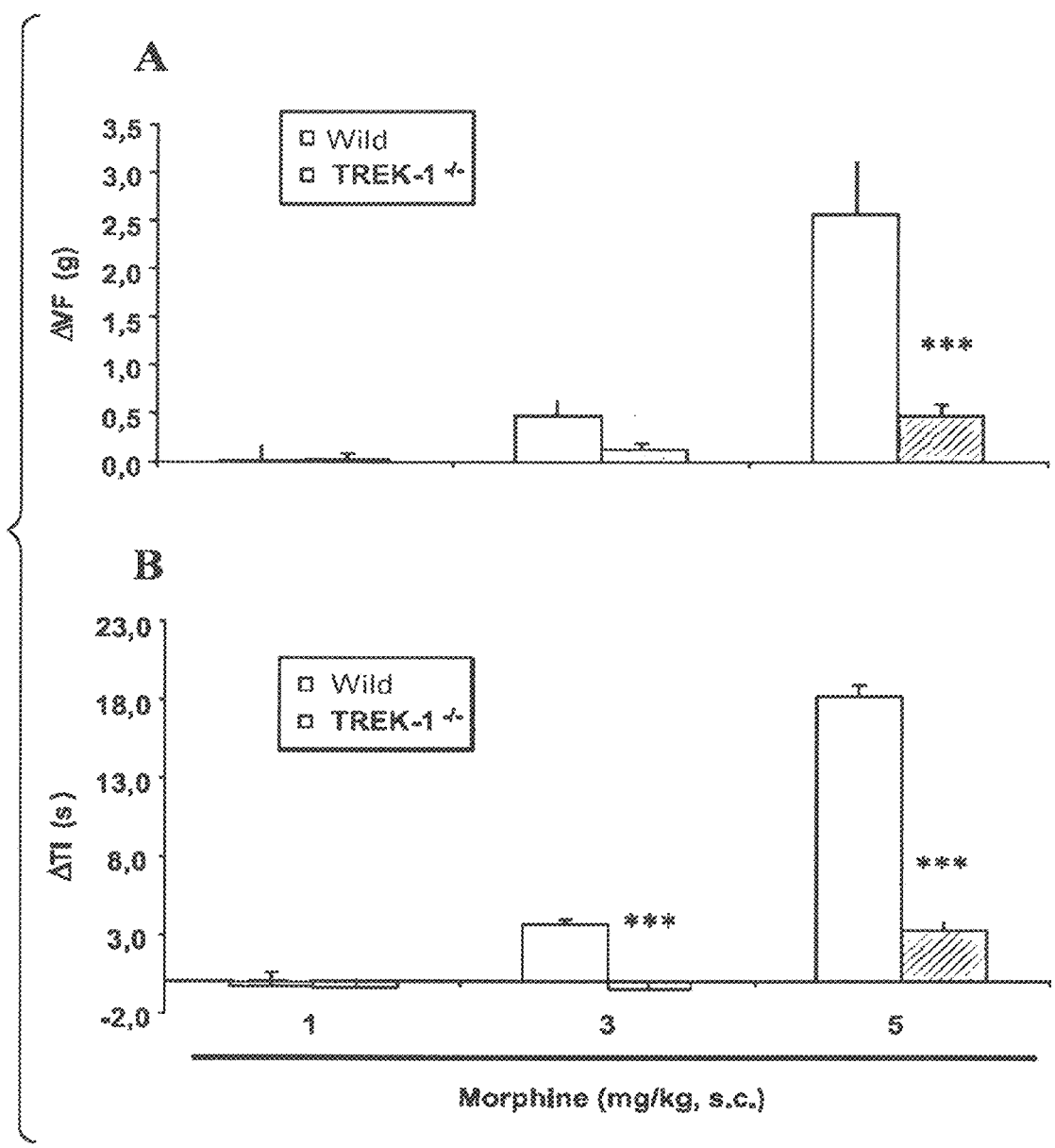
FIG. 2: Dose effect of morphine in the mechanical test of von Frey (A) or the thermal test of immersion of the tail in water at 46° C.(B) in TREK-1$^{-/-}$ and wild animals in this order. The results are expressed in changes of nociceptive thresholds relatively to the values for mice of the same genotype treated with the carrier. Regardless of the test use, statistical analysis globally shows a dose effect of morphine (F=153.3, P<0.001; F=17.5, P<0.001) and a genotype effect (F=143.2, P<0.001; F=14.2, P<0.001). The antalgic effect of morphine is reduced in TREK-1$^{-/-}$ mice as compared with wild animals (two-way Anova, post hoc Student Newman Keuls; ***, P<0.001, n=6/9 per dose and per genotype).

As the TREK-1$^{-/-}$ animals have pain thresholds, before injection of morphine or carrier, significantly lower than those of wild animals (FIG. 1A and 1B), the differences between the pre- and post-injection values were calculated for each animal, and then compared. Statistical analysis of the data, using two=way Anova, showed main effects for morphine (F=153.3; p<0,001; F=17.5; p<0,001) and the genotype (F=143.2; p<0,001; F=14.2; p<0,001), for the thermal and mechanical tests respectively. Further, while morphine increases the latency times of withdrawal of the tail in hot water at 46° C. and the mechanical pain thresholds in both genotypes, these antalgic effects of morphine are highly and significantly reduced in TREK-1$^{-/-}$ animals as compared with wild animals (FIGS. 2A and 2B).

As a conclusion, this demonstrates that the TREK-1 channels are involved in the antalgic effect of morphine.

Example 4

Influence of the Deletion of TREK-1 Channels on Constipation Induced by Morphine.

Opioid receptors are the key actors in inhibiting gastro-intestinal transit induced by morphine (Reisine and Pasternak, 1996, <<The Pharmacological Basis of Therapeutics>>, Editeurs : Hardman J G, Gilman A G, and Limbird, pages 521-555).

The impact of morphine on the transit of TREK-1$^{-/-}$ animals was therefore investigated with the goal of evaluating the influence of deletion on this undesirable effect. The effects of morphine on gastro-intestinal functions were evaluated by measuring the production of feces collected every hour for 2 hours after injection of morphine or carrier. In order to make sure that both genotypes were not different by their consumption of food and water, this consumption was measured and normalized per animal (the cages containing from 3 to 5 animals) and the data were averaged for 3 cages per genotype.

Figure 3:
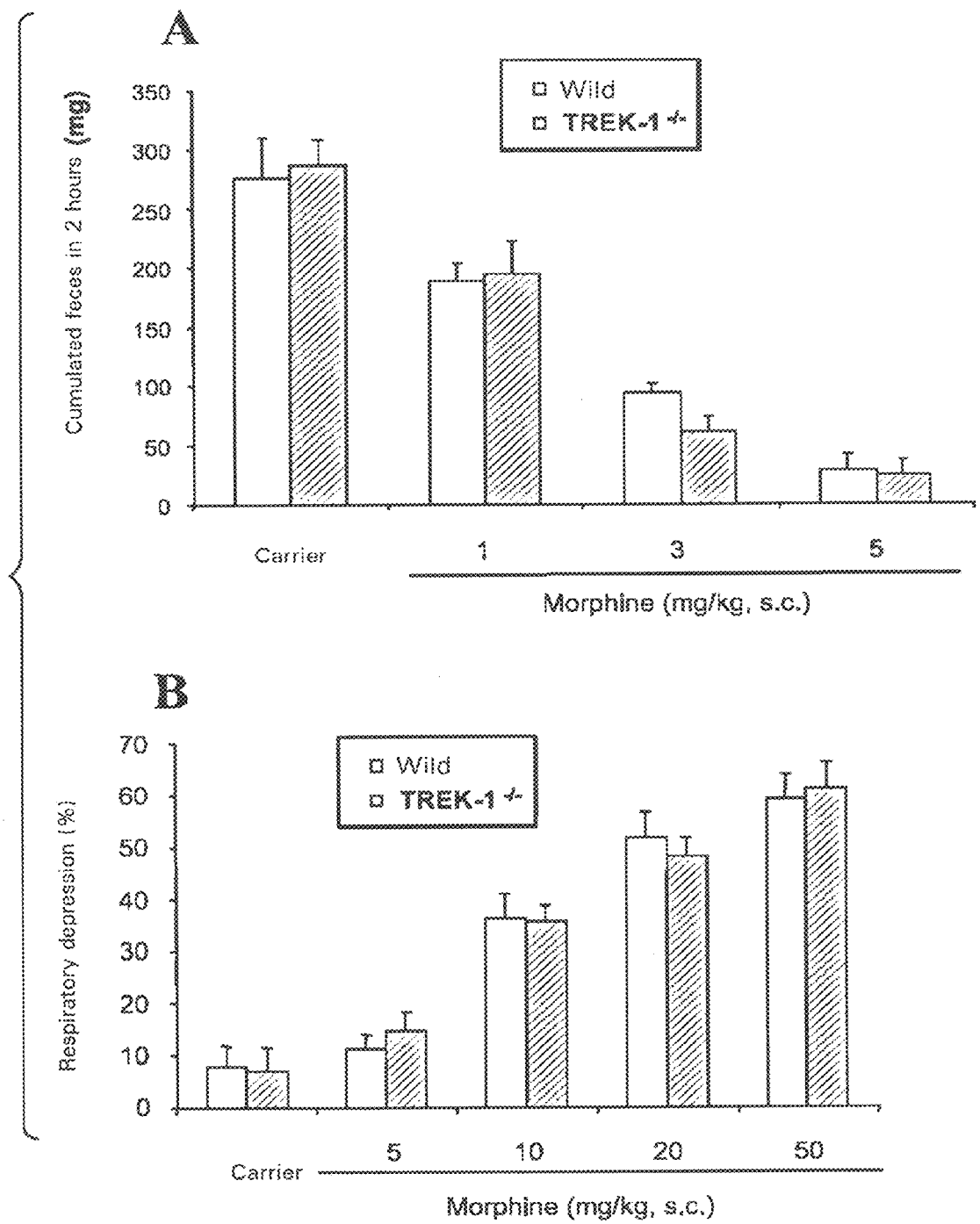
FIG. 3: (A) Amount of feces accumulated in two hours following the injection of the carrier or of morphine (1; 3; or 5 mg/kg, s.c.) in TREK-1$^{-/-}$ and wild animals. Statistical analysis globally shows a dose effect of morphine (P<0.001) but no effect of the genotype (n=5/6 per dose and genotype). (B) Respiratory depression induced by increasing doses of morphine (5; 10; 20 or 50 mg/kg, s.c.) in TREK-1$^{-/-}$ and wild animals. Statistical analysis globally shows a dose effect of morphine (P<0.001) but no effect of the genotype (n=6/8 per dose and genotype).

In the absence of treatment with morphine, no difference was observed (food consumption: wild animals, 3.17±0.23; TREK-1$^{-/-}$ animals 3.21±0.14 g/animal/24 h; water consumption: wild animals 3.69±0.41; TREK-1$^{-/-}$ animals 4.03±0.05 mL/animal/24 h). The treatment with the carrier gave an identical fecal production profile in both genotypes, suggesting that both genotypes were not different in their gastro-intestinal function under normal conditions. Morphine induces a comparable decrease in the defecation in both genotypes during the tested period as compared with treatment with the carrier (FIG. 3A).

This experiment demonstrates that the TREK-1 are not involved in the constipating effect of the morphine.

Example 5

Influence of Deletion of the TREK-1 Channels on Respiratory Depression Induced by Morphine Among the undesirable effects of morphine, the most deleterious is certainly respiratory depression, which may cause death in the case of overdoses. The respiratory depression induced by morphine also occurs via activation of opioid receptors (Santiago and Edelman, 1985 J Appl Physiol. 59:1675-85; Reisine and Pasternak, 1996, <<The Pharmacological Basis of Therapeutics>>, Editeurs : Hardman J G, Gilman A G, and Limbird, pages 521-555), further, mice for which the gene coding the µ receptor was invalidated are protected against this undesirable effect (Matthes et al., 1998 J Neurosci. 18:7285-95; Dahan et al., 2001 Anesthesiology. 94:824-32; Romberg et al., 2003 Br J Anaesth. 91:862-70). In order to determine whether the respiratory depression induced by morphine is altered by deleting the gene coding the TREK-1 channels, the breathing frequency of wild animals and TREK-$^{-/-}$ animals was measured by using a barometric plethysmograph after injection of morphine or of carrier.

The basal breathing frequency is not different in both genotypes. Further regardless of the genotype, neither the vehicle nor the morphine at a dose of 5 mg/kg influenced the breathing frequency. On the other hand regardless of the genotype, administration of morphine of doses at 10, 20 and 50 mg/kg causes a dose-dependent decrease in the breathing frequency without any difference between the genotypes (FIG. 3B).

The deletion of the gene which codes for TREK-1 does not reduce the respiratory depressive effect of morphine. The TREK-1 channel is therefore not involved in this undesirable effect.

Example 5

Role of TRAAK Channels in the Antalgic Action and the Constipating Effect of Morphine In order to test the assumption of involvement of the TRAAK channels in the antalgic action of morphine, wild and knock-out mice for the TRAAK channels (TRAAK$^{-/-}$) were used, and the effects of morphine at a dose of 5 mg/kg, injected subcutaneously were measured.

Regardless of the tests used, the mechanical sensitivity test of von Frey or the thermal test of immersion of the tail in hot water at 46° C., it was found that the TRAAK$^{-/-}$ animals had pain thresholds, before injection of morphine or carrier significantly lower than those of wild animals (FIGS. 1A and 1B).

Figure 4:
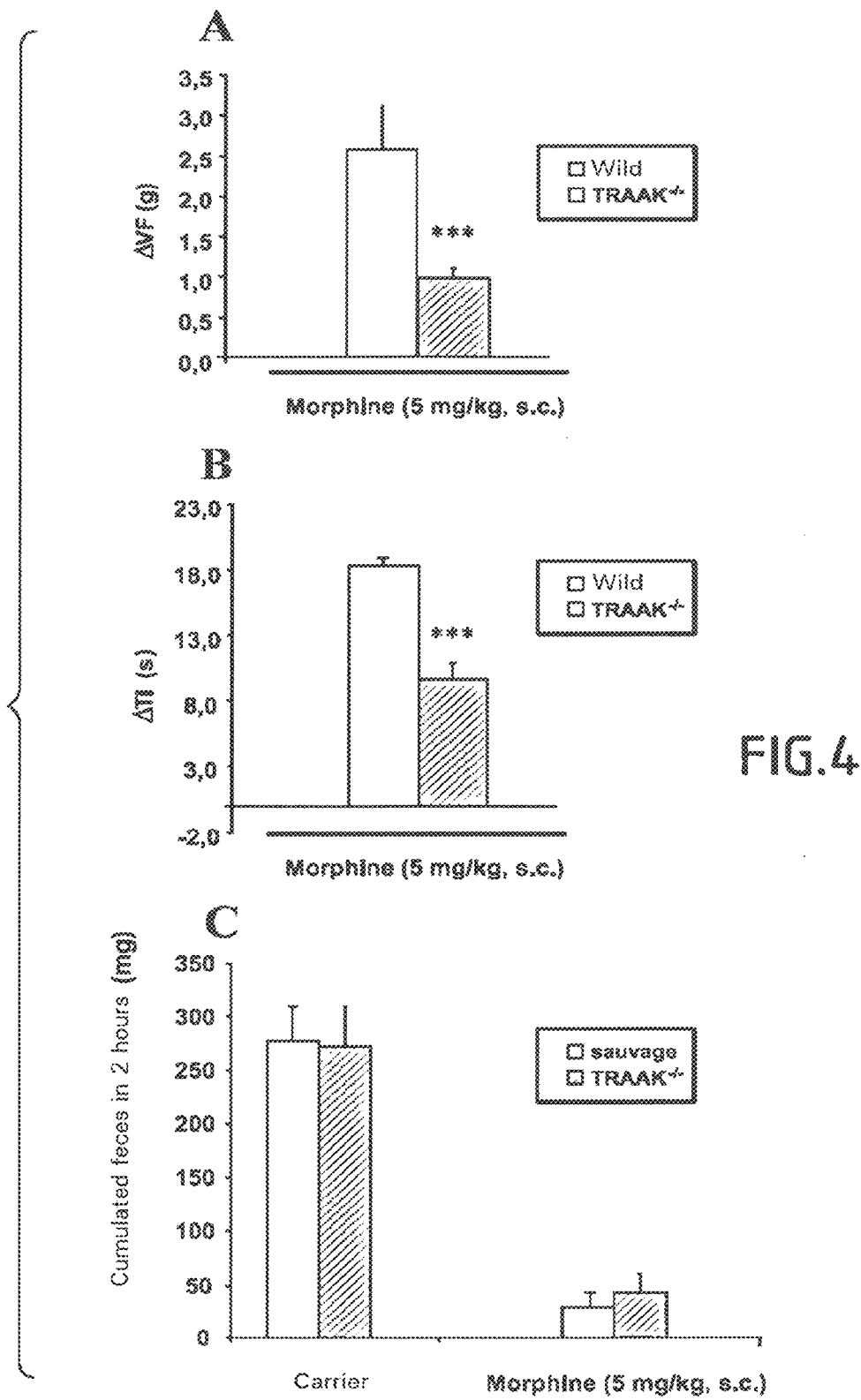
FIG. 4: Antinociceptive effect of morphine (5 mg/kg, s.c.) in the mechanical test of von Frey (A) and the thermal test of immersion of the tail in water at 46° C. (B) in TRAAK$^{-/-}$ and wild animals. The results are expressed in variations of nociceptive thresholds as compared to the values for mice of the same genotype treated with the carrier. Regardless of the tests used, statistical analysis shows that the antalgic effect of morphine is reduced in TRAAK$^{-/-}$ mice relatively to wild animals (Student's t test: ***, P<0.001, n=12/14 per group). (C) Amount of accumulated feces within two hours after injection of the carrier or of morphine (5 mg/kg, s.c.) in TRAAK$^{-/-}$ and wild animals (n=6 per dose and genotype).

The values after injection of morphine or of carrier were then measured, and the differences between the pre- and post-injection values were calculated for each animal. Statistical data analysis using a Student's t test shows that the antalgic effect of morphine is significantly decreased in TRAAK$^{-/-}$ animals as compared with wild animals (FIGS. 4A and 4B).

This result shows that the TRAAK channels are also involved in the antalgic effect of morphine.

Constipation induced by morphine in TRAAK$^{-/-}$ animals was also investigated. The effects of morphine on gastro-intestinal functions were evaluated by measuring the production of feces collected every hour for 2 hours after the injection of morphine or of carrier. In order to make sure that both genotypes were not different in their food and water consumption, this consumption was measured and normalized per animal (the cages containing from 3 to 5 animals) and the data were averaged for 3 cages per genotype.

In the absence of treatment with morphine, no difference was observed (food consumption: wild animals, 3.17±0.23; TRAAK$^{-/-}$, 3.58±0.52 g/animal/24 h; water consumption: wild animals, 3.69±0.41; TRAAK$^{-/-}$, 4.25±0.48 mL/animal/24 h). Treatment with the carrier gave an identical fecal production profile in both genotypes, suggesting that both genotypes do not differ in their gastro-intestinal function under normal conditions. Morphine induces a decrease in defecation which is comparable in both genotypes during the tested period as compared with the treatment with carrier (FIG. 4C).

This result demonstrates that the TRAAK channels are not involved in the constipating effect of morphine.

The invention claimed is:

1. A screening method for identifying an antalgic compound without any constipating and/or respiratory depressive effect, the method consisting of the following steps:
   a) providing a candidate compound;
   b) determining whether said candidate compound activates a potassium channel selected from TREK-I, TRAAK and TREK-2;
   c) measuring an antalgic effect of said candidate compound from step (b) that activates a potassium channel selected from TREK-I, TRAAK and TREK-2, in vivo on non-human model animal in terms of whether the candidate compound attenuates or abolishes pain generated during the step; and
   d) measuring the constipating and/or respiratory depressive effect of said candidate compound from step (b) that activates a potassium channel selected from TREK-I, TRAAK and TREK-2 in vivo on non-human model animal, wherein reduction of defecation is measured for the constipating effect and wherein decrease of respiratory frequency is measured for the respiratory depressive effect.

2. The screening method according to claim 1, wherein said candidate compound is a natural ligand of said potassium channel, a chemical molecule, an aptamer, a peptide, or an antibody.

3. A screening method for identifying an antalgic compound without any constipating and/or respiratory depressive effect, the method consisting of the following steps:
   a) providing a candidate compound;
   b) determining whether said candidate compound activates a potassium channel selected from TREK-I, TRAAK and TREK-2;
   c) measuring an antalgic effect of said candidate compound from step (b) that activates a potassium channel selected from TREK-I, TRAAK and TREK-2, in vivo on non-human model animal in terms of whether the candidate compound attenuates or abolishes pain generated during the step;
   d) measuring the constipating and/or respiratory depressive effect of said candidate compound from step (b) that activates a potassium channel selected from TREK-I, TRAAK and TREK-2 in vivo on non-human model animal, wherein reduction of defecation is measured for the constipating effect and wherein decrease of respiratory frequency is measured for the respiratory depressive effect; and e) selecting a compound from steps (c) and (d) that is an antalgic compound without any constipating and/or respiratory depressive effect.

4. The screening method according to claim 3, wherein said candidate compound is a natural ligand of said potassium channel, a chemical molecule, an aptamer, a peptide, or an antibody.

* * * * *